(12) United States Patent
Wang et al.

(10) Patent No.: US 10,595,785 B2
(45) Date of Patent: Mar. 24, 2020

(54) PLETHYSMOGRAPHY HEART RATE MONITOR NOISE REDUCTION USING DIFFERENTIAL SENSORS

(71) Applicant: Silicon Laboratories Inc., Austin, TX (US)

(72) Inventors: Qin Wang, East Haven, CT (US); Yahui Zhang, Austin, TX (US); David Clark, Austin, TX (US); Moshe M. Altmejd, Austin, TX (US)

(73) Assignee: Silicon Laboratories Inc., Austin, TX (US)

( * ) Notice: Subject to any disclaimer, the term of this patent is extended or adjusted under 35 U.S.C. 154(b) by 809 days.

(21) Appl. No.: 14/872,605

(22) Filed: Oct. 1, 2015

(65) Prior Publication Data

US 2017/0095211 A1 Apr. 6, 2017

(51) Int. Cl.
*A61B 5/00* (2006.01)
*A61B 5/024* (2006.01)

(52) U.S. Cl.
CPC ............ *A61B 5/721* (2013.01); *A61B 5/0082* (2013.01); *A61B 5/02427* (2013.01); *A61B 5/02433* (2013.01)

(58) Field of Classification Search
CPC ...................................................... A61B 5/721
See application file for complete search history.

(56) References Cited

U.S. PATENT DOCUMENTS

| 2003/0028085 | A1* | 2/2003 | Al-Ali | A61B 5/1455 600/323 |
| 2003/0163058 | A1* | 8/2003 | Osypka | A61B 5/02007 600/513 |
| 2007/0073121 | A1* | 3/2007 | Hoarau | A61B 5/14552 600/323 |
| 2009/0171172 | A1* | 7/2009 | Bordon | A61B 5/14551 600/324 |

(Continued)

OTHER PUBLICATIONS

Jo, Jun, et al., "Real-time Analysis of Heart Rate Variability for a Mobile Human Emotion Recognition System," Recent Advances in Electrical and Computer Engineering, WSEAS Press, 2013, pp. 162-166.

*Primary Examiner* — Rochelle D Turchen
(74) *Attorney, Agent, or Firm* — Zagorin Cave LLP

(57) ABSTRACT

An apparatus includes a first electromagnetic sensor configured to generate a first sensed signal based at least in part on detection of a first signal having a first wavelength. The apparatus includes a second electromagnetic sensor configured to generate a second sensed signal based at least in part on detection of a second signal having a second wavelength different from the first wavelength. The apparatus includes a processing circuit configured to generate a plethysmogram based at least in part on the first sensed signal and the second sensed signal. The apparatus may include a first emitter configured to emit an optical signal having the first wavelength. The apparatus may include a second emitter configured to emit a reference signal. The first wavelength may be a human-blood-sensitive and human-skin-penetrable wave- (Continued)

length and the second wavelength may be at least one of a human-blood-insensitive wavelength and a human-skin-impenetrable wavelength.

18 Claims, 4 Drawing Sheets

(56) References Cited

U.S. PATENT DOCUMENTS

| | | | | |
|---|---|---|---|---|
| 2011/0275925 | A1* | 11/2011 | Leichner | A61B 5/0422 |
| | | | | 600/407 |
| 2012/0150052 | A1 | 6/2012 | Buchheim et al. | |
| 2014/0073887 | A1* | 3/2014 | Petersen | A61B 5/0015 |
| | | | | 600/323 |
| 2015/0305674 | A1* | 10/2015 | McPherson | A61B 5/1455 |
| | | | | 600/301 |
| 2016/0018257 | A1* | 1/2016 | Mirov | A61B 5/6824 |
| | | | | 600/479 |
| 2016/0029964 | A1* | 2/2016 | LeBoeuf | A61B 5/0205 |
| | | | | 600/476 |
| 2017/0035333 | A1* | 2/2017 | Weber | A61B 5/14552 |

* cited by examiner

PLETHYSMOGRAPHY HEART RATE MONITOR NOISE REDUCTION USING DIFFERENTIAL SENSORS

BACKGROUND

Field of the Invention

The present invention is related to sensor devices in general and to wearable plethysmograph devices in particular.

Description of the Related Art

In general, a plethysmogram is a volumetric measurement of an organ. An optically determined plethysmogram, referred to as a photoplethysmogram (PPG), may be generated using a pulse oximeter that illuminates the skin and measures changes in light absorption. A conventional pulse oximeter monitors perfusion, i.e., the process of a body delivering blood to a capillary bed in biologic tissue (e.g., dermis and subcutaneous tissue of the skin). With each cardiac cycle, the heart pumps blood to the periphery of a body. Although this pressure pulse is damped by the time it reaches the skin, the pressure is sufficient to distend the arteries and arterioles in the subcutaneous tissue. A light-emitting diode (LED) may illuminate the skin with light and the amount of light either transmitted or reflected may be sensed by a photodiode to detect a change in volume caused by the pressure pulse. Each cardiac cycle may appear as a peak in the sensed signal. Motion may result in artifacts in the signal due to changes in the amount of ambient light leakage, sensor position relative to the skin, blood volume in a localized area, or physiological change due to muscle contraction. Motion-induced artifacts may introduce noise having amplitudes that are substantially greater than the amplitude of the heartbeat signal and may degrade the resulting heart rate measurement. Accordingly, improved techniques for generating a plethysmogram are desired.

SUMMARY OF EMBODIMENTS OF THE INVENTION

In at least one embodiment of the invention, an apparatus includes a first electromagnetic sensor configured to generate a first sensed signal based at least in part on detection of a first signal having a first wavelength. The apparatus includes a second electromagnetic sensor configured to generate a second sensed signal based at least in part on detection of a second signal having a second wavelength different from the first wavelength. The apparatus includes a processing circuit configured to generate a plethysmogram based at least in part on the first sensed signal and the second sensed signal. The apparatus may include a first emitter configured to emit an optical signal having the first wavelength. The first signal may be a reflected version of the optical signal. The apparatus may include a second emitter configured to emit a reference signal. The second signal may be a reflected version of the reference signal. The first emitter may be a first light-emitting diode configured to generate the optical signal and the first wavelength may be in the optical green range of wavelengths. The second emitter may be a second light-emitting diode and the second wavelength may be in one of the optical blue range of wavelengths and the infrared range of wavelengths. The first wavelength may be a human-blood-sensitive and human-skin-penetrable wavelength and the second wavelength may be at least one of a human-blood-insensitive wavelength and a human-skin-impenetrable wavelength.

In at least one embodiment of the invention, a method includes generating a plethysmogram based at least in part on a first sensed signal and a second sensed signal. The first sensed signal has a first wavelength and the second sensed signal has a second wavelength different from the first wavelength. The method may include generating the first sensed signal based at least in part on detection of a reflection of a first signal having the first wavelength. The method may include generating the second sensed signal based at least in part on detection of a reference signal having the second wavelength. The method may include emitting an optical signal. The first signal may be a reflected version of the optical signal. The method may include emitting a reference signal. The second signal may be a reflected version of the reference signal. The method may include adjusting emission of the first signal from a first power level to a second power level based at least in part on the first signal, the second signal, and a target signal-to-noise ratio for the plethysmogram. The first signal may have a wavelength in the optical green range of wavelengths and the second signal may have a wavelength in one of the optical blue range of wavelengths and the infrared range of wavelengths.

In at least one embodiment of the invention, a method includes transmitting, at a first power level, a first signal having a first wavelength. The method includes sensing a reflected signal including reflections of the first signal. The method includes sensing a second signal that is less sensitive to heart rate than the first signal. The method includes adjusting transmission of the first signal from the first power level to a second power level based at least in part on the reflected signal, the second signal, and a target signal-to-noise ratio for a plethysmogram based at least in part on the first signal and the second signal.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DETAILED DESCRIPTION

Figure 1:
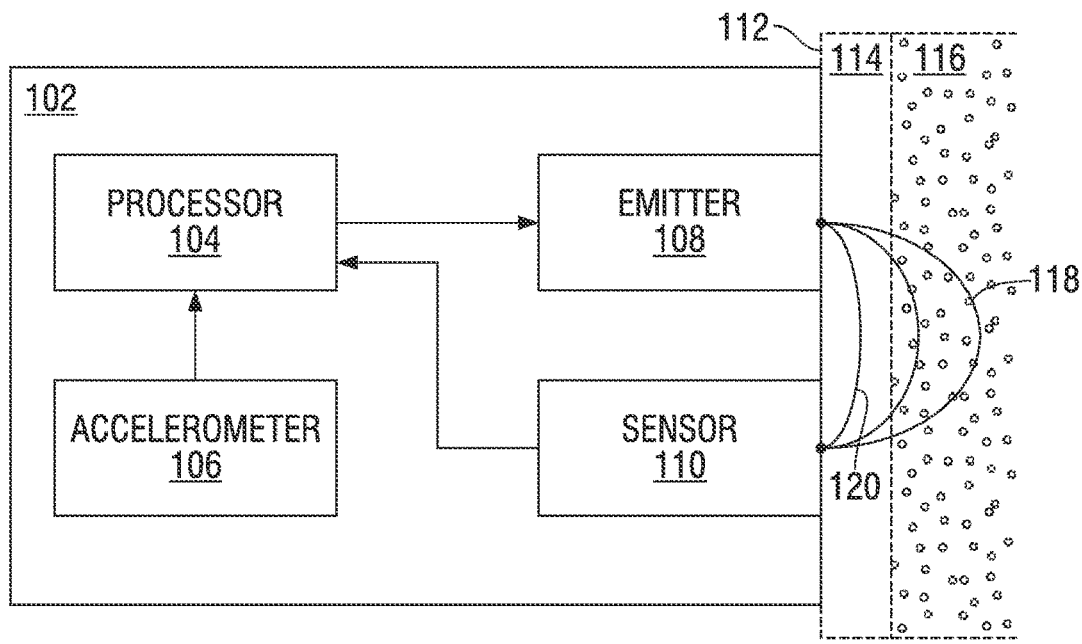
FIG. 1 illustrates a functional block diagram of a plethysmography heart rate monitor system.

Referring to FIG. 1, an exemplary plethysmography heart rate monitor system includes emitter 108, which emits an optical signal that penetrates layer 114 of tissue 112 and into subcutaneous layer 116 that includes capillaries. At least a portion of the optical signal is reflected by the capillaries and those reflections are detected using optical sensor 110, which may be a photodiode. System 102 includes accelerometer 106, an output of which is used by processor 104 to reduce or eliminate motion artifacts from the plethysmogram signal. For example, processor 104 uses signal processing techniques (e.g., fast Fourier transform techniques) to identify common frequency signals in the plethysmogram signal and the accelerometer signal and rejects those common frequency signals to reduce or eliminate motion artifacts in the plethysmogram signal. In other embodiments, processor 104 uses the output of accelerometer 106 as a reference signal to cancel noise in plethysmogram signal, similar to adaptive echo cancellation.

The weak correlation between the output of accelerometer 106 and the output of sensor 110 results in poor cancellation of the noise and a low signal-to-noise ratio of the plethysmogram signal. The output of accelerometer 106 does not directly reflect blood flow changes, physiology changes, ambient light changes, or changes in position of sensor 110 on the skin. Timing between accelerometer events and associated plethysmogram events may vary substantially, depending on the causes of the plethysmogram events. For example, plethysmogram signal changes induced by blood flow changes may occur hundreds of milliseconds, or more, after a body movement, while plethysmogram signal changes associated with ambient leakage may occur concurrently with body movement. Characterization and compensation for timing delay between body movement, as determined by the accelerometer, and resulting plethysmogram effects may be difficult or impossible to achieve. In addition, note that when the heart rate and the frequency of motion coincide, isolating a heart rate signal may not be possible.

Figure 2:
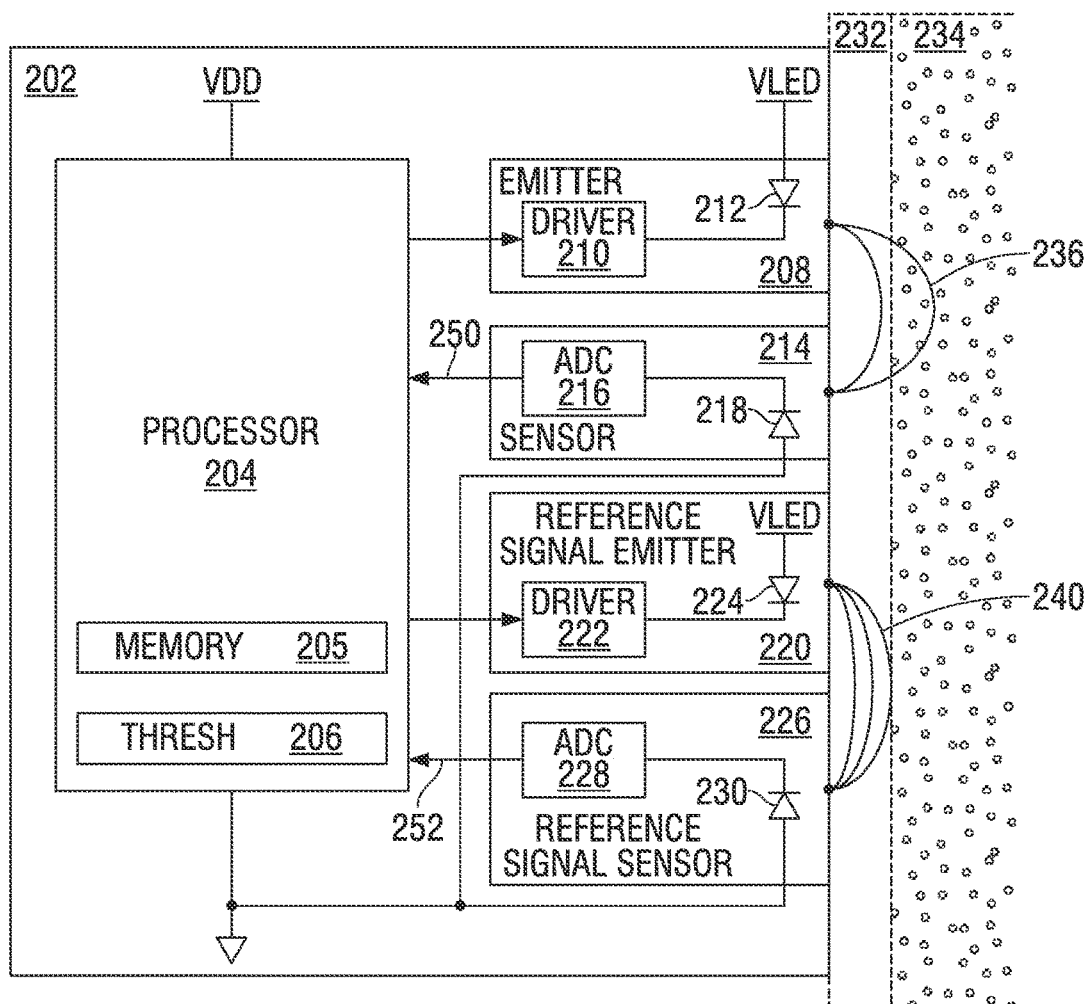
FIG. 2 illustrates a functional block diagram of a plethysmography heart rate monitor system consistent with at least one embodiment of the invention.

Referring to FIG. 2, a technique for improving a signal-to-noise ratio of a plethysmogram signal includes attenuating or removing noise components using a reference signal that is susceptible to at least some of the same noise sources as the heart rate signal, but includes little or no heart rate information. Emitter 208 generates measurement excitation signal 236, which is an electromagnetic signal (e.g., includes an optical signal having a wavelength in the optical green range of wavelengths) that penetrates body tissue through first layer 232 into subcutaneous layer 234. At least a portion of measurement excitation signal 236 is reflected by capillaries in subcutaneous layer 234 and detected using sensor 214, which may include photodiode 218. Reference signal emitter 220 emits artifact detection signal 240, which does not penetrate subcutaneous layer 234, but is subjected to at least some of the same noise sources as measurement excitation signal 236 (e.g., emitter driver noise due to power supply noise, electronic noise, ambient electromagnetic signal noise, physiological change induced noise, noise induced by small relative motion between the sensor module and the skin, etc.). Artifact detection signal 240 is an electromagnetic signal that has less sensitivity to heart rate than measurement excitation signal 236 and thus contains less heart rate information. Accordingly, reflected versions of artifact detection signal 240 contain little or no heart rate signal information but include noise information comparable to the noise information in reflected versions of measurement excitation signal 236.

Figure 3:
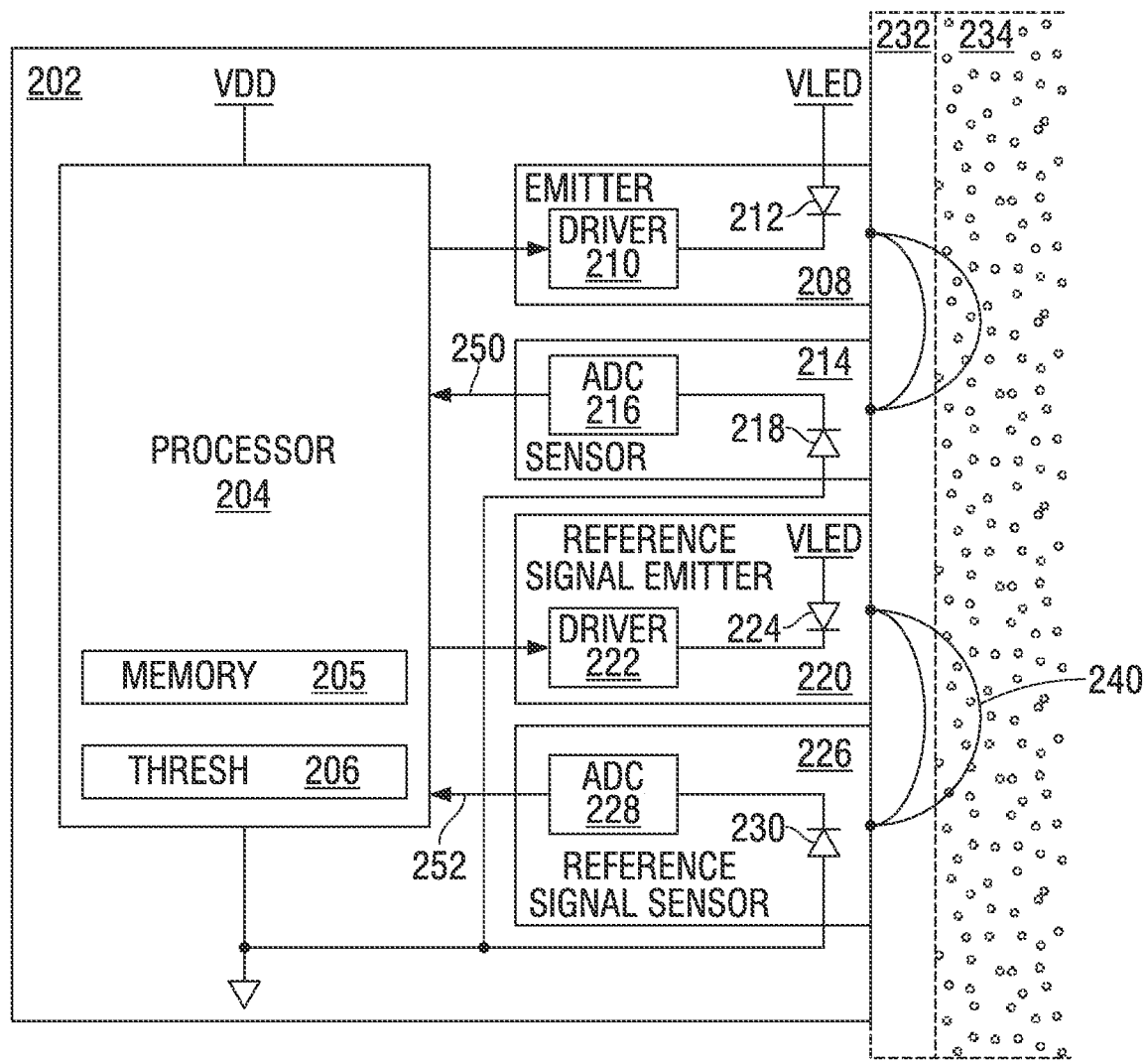
FIG. 3 illustrates a functional block diagram of a plethysmography heart rate monitor system consistent with at least one embodiment of the invention.

In at least one embodiment, artifact detection signal 240 includes an optical signal having a wavelength in the optical blue range of wavelengths. The optical blue wavelength range signal does not penetrate layer 232 well, thus reflected versions of artifact detection signal 240 will have little or no heart rate information. Referring to FIG. 3, in other embodiments, artifact detection signal 240 includes signals having other wavelengths, e.g., a signal having a wavelength in the infrared range of wavelengths. Infrared wavelength range signals penetrate layer 232, but are not well absorbed by subcutaneous layer 234, thus reflected versions of artifact detection signal 240 having infrared wavelengths will have little or no heart rate information. Although measurement excitation signal 236 and artifact detection signal 240 travel through the same layers of tissue, the different wavelengths result in different losses on entry and exit of the tissue, different losses in diffusion through the tissue, and different amounts of modulation of the signal transmission through the tissue. Referring to FIGS. 2 and 3, in other embodiments, measurement excitation signal 236 is another electromagnetic signal that is sensitive to heart rate and artifact detection signal 240 is another electromagnetic signal that is insensitive to heart rate or has less modulation of signal transmission through the tissue by heart rate, but susceptible to the same noise sources as measurement excitation signal 236.

In at least one embodiment, the position of reference signal emitter 220 and a wavelength of artifact detection signal 240 generated by reference signal emitter 220 are selected to reduce or eliminate the sensitivity of digital reference signal 252 to heart rate. The position of emitter 208 and the wavelength of the measurement excitation signal 236 generated by emitter 208 are selected to cause digital signal 250 to be sensitive to heart rate. Distance of separation between emitter 208 and sensor 214 may be predetermined for a target heart rate signal detection level. Distance of separation between reference signal emitter 220 and reference signal sensor 226 may be predetermined for a target reference signal detection level. Emitter 208 may include driver 210 and light-emitting diode 212. In at least one embodiment, rather than use light-emitting diode 212, a vertical cavity surface-emitting laser (VCSEL) or other electromagnetic signal may be used instead. Reference signal emitter 220 may include driver 222 and light-emitting diode 224. In at least one embodiment, rather than use light-emitting diode 224, a vertical cavity surface-emitting laser or other electromagnetic signal emitter is included instead.

Sensor 214 may include electromagnetic sensor 218, which may include a photodiode. Sensor 214 is configured to sense the reflected version of measurement excitation signal 236 and provides a digital version of the signal to processor 204. Sensor 214 may include analog-to-digital converter 216, which provides digital reference signal 250 to processor 204. Reference signal sensor 226 may include electromagnetic sensor 230, which may include a photodiode. Reference signal sensor 226 is configured to sense the reflected version of signal 240 and provides a digital version of the signal, digital reference signal 252 to processor 204. Reference signal sensor 226 may include analog-to-digital converter 228, which provides digital reference signal 252 to processor 204.

Signal processor 204 uses digital reference signal 252, which is based on the reflected versions of artifact detection signal 240, to remove noise from digital signal 250, which is based on the reflected versions of measurement excitation signal 236. Since measurement excitation signal 236 and artifact detection signal 240 are signals having wavelengths relatively close in the electromagnetic spectrum and emitter 208 and reference signal emitter 220 are co-located, measurement excitation signal 236 and artifact detection signal 240 have a strong correlation. Noise cancellation using a reflected version of artifact detection signal 240 results in a plethysmogram signal having a higher signal-to-noise ratio than a signal-to-noise ratio achieved by systems that attempt to cancel noise using an accelerometer signal that is weakly correlated to a signal including heart rate information (e.g., system 102 of FIG. 1).

Conventional noise cancellation techniques used by typical plethysmograph systems that use an accelerometer signal are relatively fragile and complex, and may require frequent updates for new application environments due to weak correlation between the reference signal and the signal including heart rate information. Referring back to FIG. 2, plethysmograph system 202 is more robust across various application environments than typical plethysmograph systems due to the higher correlation between signal 250 and digital reference signal 252 as compared to the signals used to cancel noise in the typical plethysmogram system. Moreover, since digital signal 250 and digital reference signal 252 of plethysmograph system 202 have a strong correlation, conventional echo cancellation techniques (e.g., classical time-domain least-mean squared echo cancellation techniques) may be used to process those signals.

Figure 5:
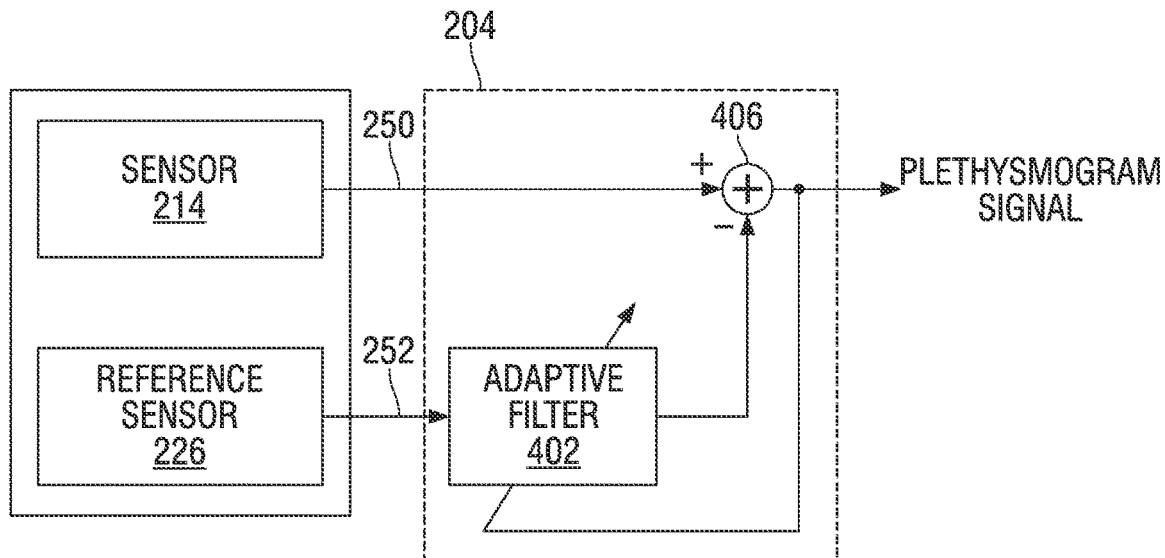
FIG. 5 illustrates a functional block diagram of portions of a plethysmography heart rate monitor system consistent with at least one embodiment of the invention.

Referring to FIG. 5, an exemplary adaptive echo cancellation technique implemented by processor 204 includes generating an estimate of the motion artifacts from the reference signal 252 using adaptive filter 402 and subtracting the estimate from measurement excitation signal 240 (e.g., using difference module 406) to reduce the motion artifacts, as illustrated in FIG. 5. Note that although adaptive filter 402 and difference module 406 may be implemented using dedicated integrated circuit modules, in at least one embodiment, processor 204 is a digital signal processor programmed with software to execute an adaptive filtering subroutine and with software to execute a difference computation subroutine. Software (which includes firmware), as described herein, may be encoded in memory 205, which may include at least one tangible computer readable medium. As referred to herein, a tangible computer-readable medium includes at least a disk, tape, or other magnetic, optical, or electronic storage medium.

Referring back to FIG. 2, in general, improving the signal-to-noise ratio of a plethysmogram signal, may improve heart rate monitor performance in applications that typically have poor performance, e.g., applications having low reflected signal levels. For example, a heart rate monitor in use by a thin body, a body having a dark skin tone, or a body having low body temperature, typically does not achieve a high signal-to-noise ratio even when the body is stationary. Body motion further degrades that already low signal-to-noise ratio. By reducing noise in the plethysmogram signal, the signal-to-noise ratio of a poor plethysmogram signal may improve and be degraded less by body motion.

Conventional wearable plethysmograph devices often include different activity modes (e.g., running mode or idling mode) selectable by a user prior to initiating a heart rate (or other) monitor measurement. However, since plethysmograph system 202 cancels noise using a technique that is motion independent, unlike those conventional plethysmograph systems, plethysmograph system 202 needs no such activity adjustments and such modes and associated facilities may be eliminated. Since the same noise cancellation technique may be used regardless of user activity and the user need not regularly change modes according to activity, plethysmograph system 202 may be easier to use than a conventional plethysmograph system.

In addition, plethysmograph system 202 is not timing-sensitive since digital signal 250 and digital reference signal 252 have similar timing. Since plethysmograph system 202 increases the signal-to-noise ratio of the resulting plethysmogram signal as compared to a conventional system, light-emitting diode 212 of emitter 208 may not need to be driven as strongly as a light-emitting diode of a conventional system, thus reducing energy consumption of plethysmograph system 202 as compared to the conventional system. In addition, since plethysmograph system 202 reduces or eliminates noise in a plethysmogram signal, driver 210 need not be a low noise driver, thereby reducing or eliminating the need for high-precision components, reducing driver size, and, thus, reducing the cost of plethysmograph system 202 as compared to a corresponding driver in a conventional system. Since the plethysmogram of plethysmograph system 202 is motion independent, plethysmograph system 202 may not experience reduced signal-to-noise ratio in applications where the rate of motion (e.g., the step rate) overlaps with, or aliases, the heart rate.

Figure 4:
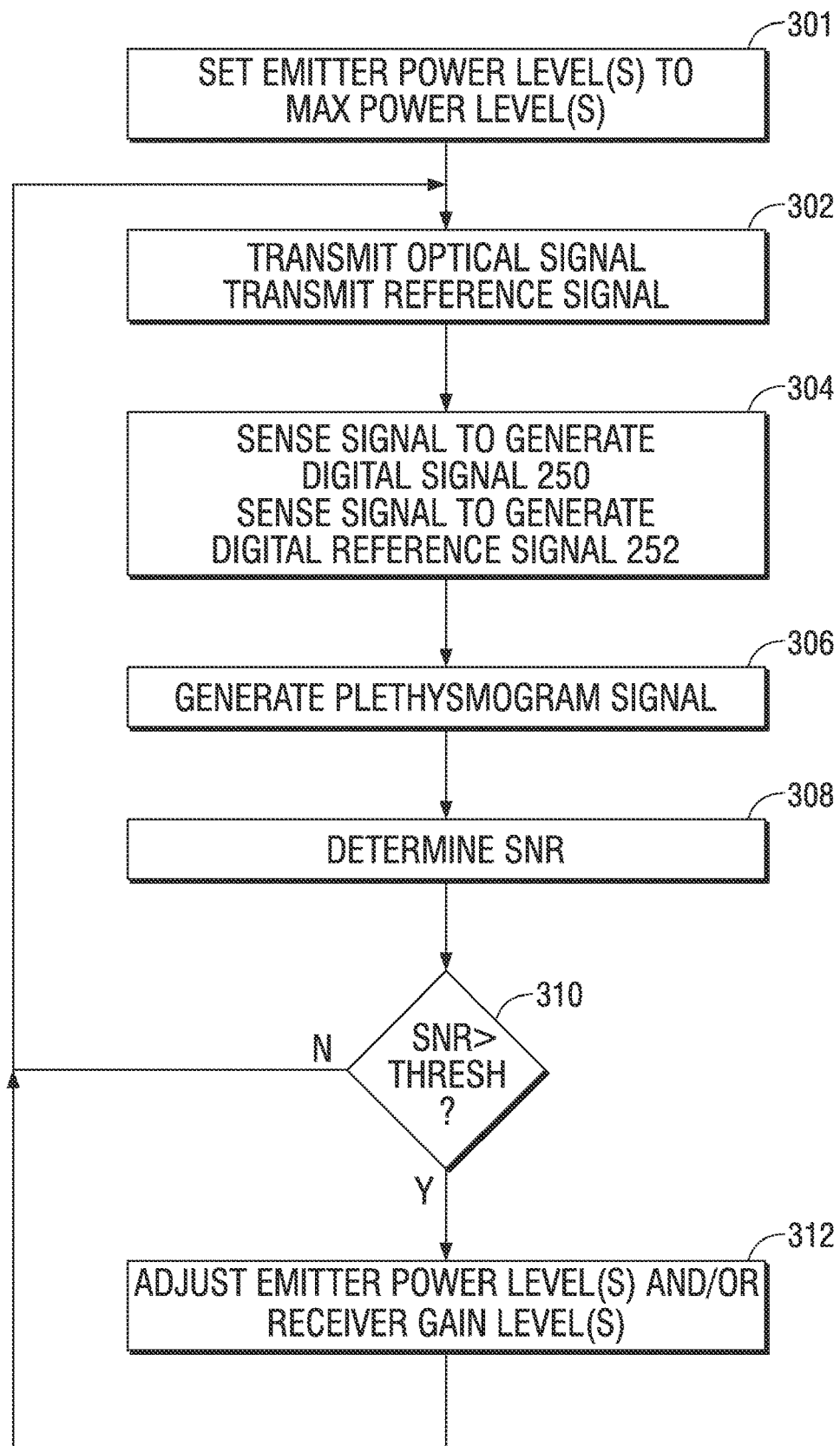
FIG. 4 illustrates exemplary information and control flows for the plethysmography heart rate monitor system of FIG. 2 consistent with at least one embodiment of the invention.

Referring to FIGS. 2 and 4, in at least one embodiment of plethysmograph system 202, processor 204 is configured to adjust a transmission power level of emitter 208 from a first power level to a second power level based on a target signal-to-noise ratio for a plethysmogram generated using digital signal 250 and digital reference signal 252. For example, processor 204 configures emitter 208 to transmit measurement excitation signal 236 at a maximum value of a first power level and configures reference signal emitter 220 to transmit artifact detection signal 240 at a maximum value of a second power level (301). Note that processor 204 may also configure other elements of plethysmograph system 202. For example, processor 204 may set a gain or sensitivity level of analog-to-digital converter 216, photodiode 218, or other element of sensor 214 to levels that correspond to the first power level and may set a gain or sensitivity level of analog-to-digital converter 228, photodiode 230, or other element of reference signal sensor 226 to levels that correspond to the second power level. The first and second power levels may be the same or may vary and may be selected according to the wavelength of measurement excitation signal 236 or the wavelength of artifact detection signal 240 and indicators thereof stored in memory 205. Emitter 208 transmits measurement excitation signal 236 at the first power level and reference signal emitter 220 transmits artifact detection signal 240 at the second power level (302). Plethysmograph system 202 senses reflections of measurement excitation signal 236 and generates digital signal 250 based thereon. Plethysmograph system 202 senses reflections of artifact detection signal 240 and generates digital reference signal 252 based thereon (304).

Processor 204 generates the plethysmogram signal, e.g., using digital signal processing techniques such as adaptive noise cancellation using digital reference signal 252 and digital signal 250, as described above (306). Processor 204 determines a signal-to-noise ratio of the plethysmogram signal (308). Processor 204 compares the signal-to-noise ratio to a threshold signal-to-noise ratio, which may be stored in storage location 206 (310). The threshold signal-to-noise ratio may be predetermined by any suitable technique (e.g., hardwired, received from a user using an interface to plethysmograph system 202, read by processor 204 from a non-volatile storage element and stored in storage location 206, etc.). If the signal-to-noise ratio of the plethysmogram signal exceeds the threshold signal-to-noise ratio, then processor 204 may adjust (e.g., decrease) the first power level, the second power level, or combination thereof, and may adjust corresponding receiver gain levels (312). In at least one embodiment of plethysmograph system 202, if the signal-to-noise ratio of the plethysmogram signal falls below a second threshold signal-to-noise ratio, then processor 204 may adjust the first power level, the second power level, receiver gain levels, or combination thereof, toward the maximum levels or other predetermined levels, if not already at those levels. In addition, note that the information and control flow of FIG. 4 may be adapted to implement hysteresis using different threshold levels to determine when to increase or decrease the emitter power levels and corresponding receiver gain levels.

Figure 6:
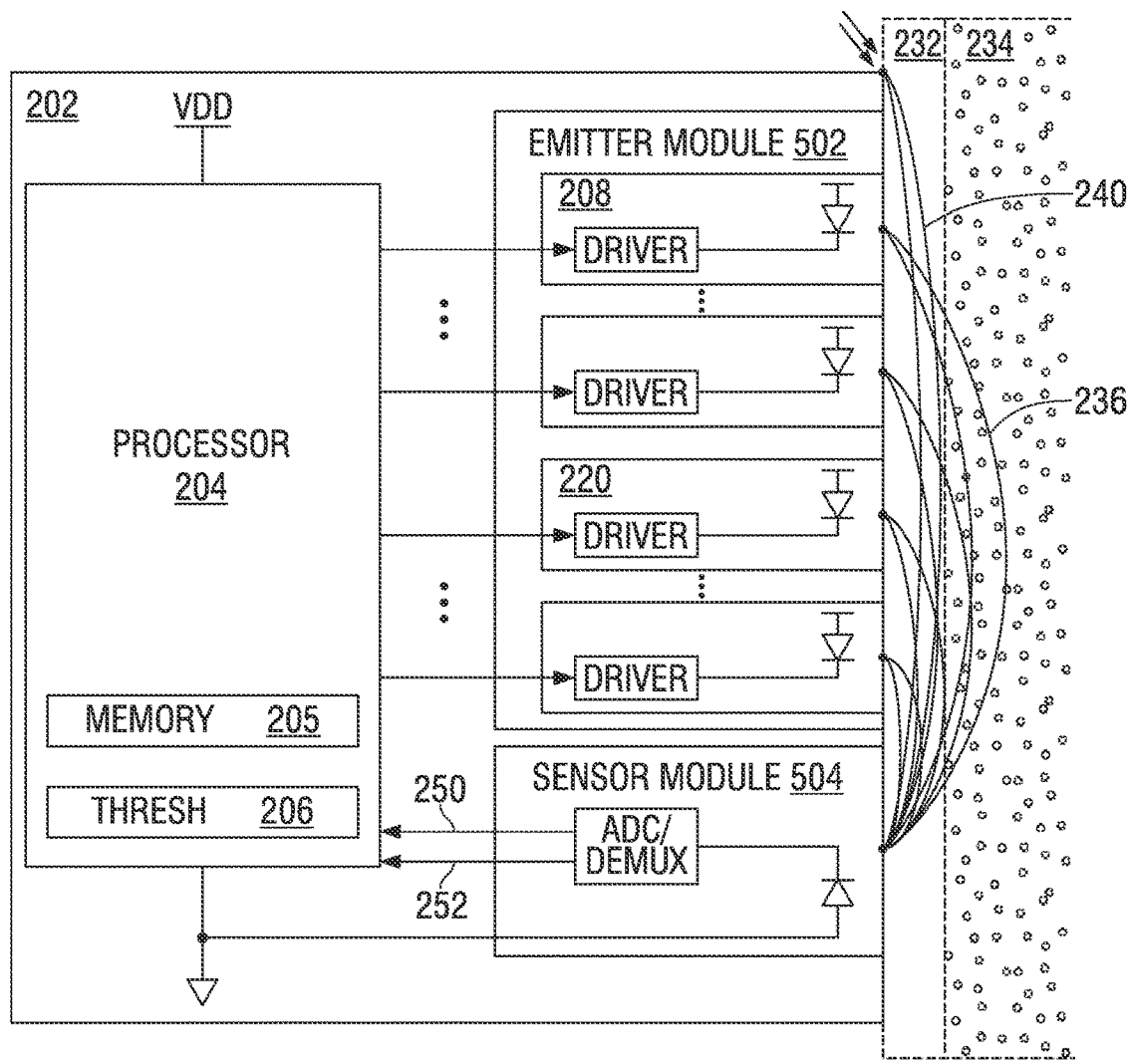
FIG. 6 illustrates a functional block diagram of a plethysmography heart rate monitor system consistent with at least one embodiment of the invention.

Referring to FIGS. 2 and 6, although plethysmograph system 202 has been described as including emitter 208, reference signal emitter 220, sensor 214 and reference signal sensor 226, the techniques described herein may be adapted to various embodiments of plethysmograph system 202. For example, measurement excitation signal 236 may be generated using emitter 208 and additional emitters, each including at least one driver and at least one light-emitting diode circuit that generate the measurement excitation signal including one or more signals having a wavelength or a combination of signals having a range of wavelengths, which may be selected based on the intended application (e.g., body part, skin type, and design preference). Similarly, artifact detection signal 240 may be generated using reference signal emitter 220 and additional emitters, each including at least one driver and at least one light-emitting diode circuit that generate artifact detection signal 240 including one or more signals having a wavelength or combination of signals having a range of wavelengths that are less sensitive to heart rate in the target tissue. For example, artifact detection signal 240 may include wavelengths shorter than the wavelength(s) of measurement excitation signal 236 and that are indicative of surface conditions and wavelength(s) longer than the wavelength(s) of measurement excitation signal 236 and that are absorbed less by blood and are not modulated by heart rate but are indicative of loss on skin entry and its variation. The multiple emitter circuits of emitter module 502 may be independently controllable by processor 204 or some may be configured to receive the same control signals. In at least one embodiment of plethysmograph system 202, reference signal emitter 220 is excluded and only ambient light is used as artifact detection signal 240. The amount of ambient light received by reference signal sensor 226 of FIG. 2 or sensor module 504 of FIG. 6 may be related to the same noise sources as measurement excitation signal 236 but is heart rate insensitive.

In at least one embodiment of plethysmograph system 202, emitter 208 and reference signal emitter 220 have different displacements with respect to corresponding sensors or sensor module 504 and may transmit using time-multiplexed time slots. The displacements relative to corresponding sensors may increase the sensitivity of measurement excitation signal 236 generated by emitter 208 to heart rate and decrease sensitivity to heart rate of artifact detection signal 240, even in embodiments of plethysmograph system 202 where emitter 208 and reference signal emitter 220 generate signals having the same wavelengths.

In at least one embodiment of plethysmograph system 202, rather than using multiple sensors (e.g., sensor 214 and reference signal sensor 220), a sensor module uses a time-multiplexed sensor to generate both digital signal 250 and digital reference signal 252. For example, sensor module 504 includes one physical sensor that detects signals having the measurement excitation signal wavelength or measurement excitation signal range of wavelengths during a first time slot of alternating time slots and detects signals having the artifact detection signal wavelengths or artifact detection signal range of wavelengths during a second time slot of the alternating time slots. An analog-to-digital converter digitizes and demultiplexes the signals and provides digital signal 250 and digital reference signal 252 to processor 204.

While circuits and physical structures have been generally presumed in describing embodiments of the invention, it is well recognized that in modern semiconductor design and fabrication, physical structures and circuits may be embodied in computer-readable descriptive form suitable for use in subsequent design, simulation, test or fabrication stages. Structures and functionality presented as discrete components in the exemplary configurations may be implemented as a combined structure or component. Various embodiments of the invention are contemplated to include circuits, systems of circuits, related methods, and tangible computer-readable medium having encodings thereon (e.g., VHSIC Hardware Description Language (VHDL), Verilog, GDSII data, Electronic Design Interchange Format (EDIF), and/or Gerber file) of such circuits, systems, and methods, all as described herein, and as defined in the appended claims.

The description of the invention set forth herein is illustrative, and is not intended to limit the scope of the invention as set forth in the following claims. For example, while the invention has been described in embodiments of a heart rate monitor system, one of skill in the art will appreciate that the teachings herein can be utilized with systems that use measurements of blood flow to the skin for monitoring breathing, hypovolemia, and other circulatory conditions. Variations and modifications of the embodiments disclosed herein, may be made based on the description set forth herein, without departing from the scope and spirit of the invention as set forth in the following claims.

What is claimed is:

1. An apparatus comprising:
a first electromagnetic sensor configured to generate a first sensed signal based at least in part on detection of a first signal having a first wavelength;
a second electromagnetic sensor configured to generate a second sensed signal based at least in part on detection of a second signal having a second wavelength different from the first wavelength;
a processing circuit configured to generate a plethysmogram based at least in part on the first sensed signal and the second sensed signal;
a first emitter configured to emit an optical signal having the first wavelength, the first signal being a reflected version of the optical signal; and
a second emitter configured to emit a reference signal, the second signal being a reflected version of the reference signal, the first emitter being positioned adjacent to the first electromagnetic sensor and the second emitter being positioned adjacent to the second electromagnetic sensor,
wherein the processing circuit is configured to adjust a first power level of the first emitter using hysteresis based on a signal-to-noise ratio of the plethysmogram, a threshold signal-to-noise signal level, and an additional threshold signal-to-noise signal level.

2. The apparatus as recited in claim 1, wherein the first emitter is a first light-emitting diode configured to generate the optical signal and the first wavelength is in an optical green range of wavelengths and the second emitter is a second light-emitting diode and the second wavelength is in an infrared range of wavelengths.

3. The apparatus as recited in claim 2, wherein the reference signal is susceptible to at least some of the same noise sources as the first signal and insusceptible to heart rate signal variations.

4. The apparatus as recited in claim 1, wherein the first wavelength is human-blood-sensitive and human-skin-penetrable and the second wavelength is human-blood-insensitive and human-skin-penetrable.

5. The apparatus as recited in claim 1, wherein the first wavelength is heart-rate-sensitive and the second wavelength is heart-rate-insensitive.

6. The apparatus as recited in claim 1, wherein the first electromagnetic sensor comprises a photodiode and the second electromagnetic sensor comprises a second photodiode.

7. The apparatus as recited in claim 1, wherein a first signal-to-noise ratio of the plethysmogram is greater than a second signal-to-noise ratio of the first sensed signal.

8. The apparatus, as recited in claim 1, wherein the first emitter is positioned to obtain a predetermined sensitivity of the first sensed signal to heart rate and the second emitter is positioned to obtain insensitivity of the second sensed signal to the heart rate.

9. The apparatus, as recited in claim 8, wherein the first emitter, the second emitter, the first electromagnetic sensor, and the second electromagnetic sensor are positioned colinearly.

10. An apparatus comprising:
a first emitter configured to emit an optical signal having a first wavelength that is human-blood-sensitive and human-skin-penetrable; and
a second emitter configured to emit a reference signal having a second wavelength that is in an infrared range of wavelengths;
a first electromagnetic sensor configured to generate a first sensed signal based at least in part on detection of a first signal having the first wavelength;
a second electromagnetic sensor configured to generate a second sensed signal based on detection of a second signal having the second wavelength; and
a processing circuit configured to generate a plethysmogram based at least in part on the first sensed signal and the second sensed signal,
wherein the processing circuit is configured to adjust a first power level of the first emitter or a second power level of the second emitter based on the plethysmogram and a threshold signal-to-noise signal level, and
wherein the processing circuit is configured to adjust the first power level using hysteresis based on a signal-to-noise ratio of the plethysmogram, the threshold signal-to-noise signal level, and an additional threshold signal-to-noise signal level.

11. The apparatus, as recited in claim 10, wherein the first emitter is positioned to obtain a predetermined sensitivity of the first sensed signal to heart rate and the second emitter is positioned to obtain insensitivity of the second sensed signal to heart rate.

12. The apparatus, as recited in claim 10, wherein the first emitter, the second emitter, the first electromagnetic sensor, and the second electromagnetic sensor are positioned colinearly.

13. The apparatus, as recited in claim 10, wherein the first emitter is configured to have a maximum value of the first power level and the processing circuit is configured to decrease the first power level in response to the signal-to-noise ratio of the plethysmogram exceeding the threshold signal-to-noise signal level.

14. The apparatus, as recited in claim 13, wherein after decreasing the first power level, the processing circuit is configured to increase the first power level in response to the signal-to-noise ratio of the plethysmogram being below the threshold signal-to-noise signal level.

15. The apparatus, as recited in claim 10, wherein the first emitter is disposed a first predetermined distance from the first electromagnetic sensor and the second emitter is disposed a second predetermined distance from the second electromagnetic sensor, the first predetermined distance corresponding to a target heart rate signal detection level and the second predetermined distance corresponding to a target reference signal detection level.

16. The apparatus, as recited in claim 1, wherein the first emitter is configured to have a maximum value of the first power level and the processing circuit is configured to decrease the first power level in response to the signal-to-noise ratio of the plethysmogram exceeding the threshold signal-to-noise signal level.

17. An apparatus comprising:
a first electromagnetic sensor configured to generate a first sensed signal based at least in part on detection of a first signal having a first wavelength;
a second electromagnetic sensor configured to generate a second sensed signal based at least in part on detection of a second signal having a second wavelength different from the first wavelength;
a processing circuit configured to generate a plethysmogram based at least in part on the first sensed signal and the second sensed signal;
a first emitter configured to emit an optical signal having the first wavelength, the first signal being a reflected version of the optical signal; and
a second emitter configured to emit a reference signal, the second signal being a reflected version of the reference signal, the first emitter being positioned adjacent to the first electromagnetic sensor and the second emitter being positioned adjacent to the second electromagnetic sensor,
wherein the processing circuit is configured to adjust a first power level of the first emitter or a second power level of the second emitter based on the plethysmogram and a threshold signal-to-noise signal level,
wherein the first emitter is configured to have a maximum value of the first power level and the processing circuit is configured to decrease the first power level in response to a signal-to-noise ratio of the plethysmogram exceeding the threshold signal-to-noise signal level,
wherein after decreasing the first power level, the processing circuit is configured to increase the first power level in response to the signal-to-noise ratio of the plethysmogram being below the threshold signal-to-noise signal level.

18. The apparatus, as recited in claim 1, wherein the first emitter is disposed a first predetermined distance from the first electromagnetic sensor and the second emitter is disposed a second predetermined distance from the second electromagnetic sensor, the first predetermined distance corresponding to a target heart rate signal detection level and the second predetermined distance corresponding to a target reference signal detection level.

* * * * *